United States Patent
Rogosnitzky

(10) Patent No.: US 9,855,204 B1
(45) Date of Patent: *Jan. 2, 2018

(54) METHODS AND COMPOSITIONS FOR TREATING ANDROGENETIC ALOPECIA

(71) Applicant: Moshe Rogosnitzky, Kiryay Yearim (IL)

(72) Inventor: Moshe Rogosnitzky, Kiryay Yearim (IL)

(*) Notice: Subject to any disclaimer, the term of this patent is extended or adjusted under 35 U.S.C. 154(b) by 0 days.

This patent is subject to a terminal disclaimer.

(21) Appl. No.: 15/387,676

(22) Filed: Dec. 22, 2016

Related U.S. Application Data

(63) Continuation-in-part of application No. 15/164,908, filed on May 26, 2016, now Pat. No. 9,561,224.

(60) Provisional application No. 62/166,833, filed on May 27, 2015.

(51) Int. Cl.
 *A61K 8/49* (2006.01)
 *A61K 8/97* (2017.01)
 *A61Q 7/00* (2006.01)

(52) U.S. Cl.
 CPC .............. *A61K 8/49* (2013.01); *A61K 8/97* (2013.01); *A61Q 7/00* (2013.01); *A61K 2800/87* (2013.01); *A61K 2800/92* (2013.01)

(58) Field of Classification Search
 CPC .............. A61K 31/4745; A61K 9/0053; A61K 31/185; A61K 31/197; A61K 31/198; A61K 31/355; A61K 31/4188; A61K 31/4415; A61K 31/473; A61K 31/506; A61K 31/51; A61K 31/525; A61K 31/714; A61K 33/04; A61K 33/30; A61K 33/34; A61K 36/00

USPC .......................................................... 514/279
 See application file for complete search history.

(56) References Cited

U.S. PATENT DOCUMENTS

2007/0254946 A1* 11/2007 Nakaoji .................. A61K 8/498
 514/456

FOREIGN PATENT DOCUMENTS

| EP | 0011654 A1 | 6/1980 |
| WO | WO 2016/199147 | 12/2016 |

OTHER PUBLICATIONS

Novak: Alopecia: Possible Causes and Treatments, Particularly in Captive Nonhuman Primates (2009) Comparative Medicine 59(1):18-26.
Cepharanthine Product Insert (2009) Kusuri-no-Shiori; Japan [English Translation].
Cepharanthine Product Insert (1995) Kakenshoyaku Inc.; Japan [English Translation].
Japanese version of 3a.
Tsuboi Guidelines for the management of androgenetic alopecia(2010) J. Dermatology(2012) 39:113-120.
Notice of allowance in U.S. Appl. No. 15/164,908.
Wang, Li Qiang & Ma, Ming, Preparation and Clinical Application of Persantine Eye Drops, Chinese Journal of Hospital Pharmacy, Dec. 1997, p. 138-9, vol. 17(3), China (Chinese. Language publication submitted together with English translation).

* cited by examiner

*Primary Examiner* — Yevegeny Valenrod
(74) *Attorney, Agent, or Firm* — IPAttitude Ltd.; S. Yarus

(57) ABSTRACT

A treatment method including: (a) identifying a subject in need of treatment for androgenic alopecia (AGA), and (b) orally administering a physiologically effective amount of cepharanthine (CEP) to the subject according to a dosage regimen.

20 Claims, No Drawings

METHODS AND COMPOSITIONS FOR TREATING ANDROGENETIC ALOPECIA

RELATED APPLICATIONS

This application is a continuation in part (CIP) of U.S. Ser. No. 15/164,908 filed on May 26, 2016 and having the same title and inventor as the present application which is currently pending;

which claimed benefit under 35 U.S.C. §119(e) of provisional application U.S. 62/166,833 filed 27, May 2015 and entitled "Methods and Compositions for Treating Androgenetic Alopecia";

each of which is fully incorporated herein by reference.

FIELD OF THE INVENTION

The various embodiments of the invention are in the field of treatments for baldness.

BACKGROUND

The alopecia types described below can affect men, women and/or children. Androgenetic alopecia rarely affects children.

Tinea capitis (ringworm of the scalp) is a disease caused by a superficial fungal infection of the skin of the scalp, eyebrows, and eyelashes, with a propensity for attacking hair shafts and follicles. The disease is considered to be a form of superficial mycosis or dermatophytosis. Several other names are used when referring to this infection, including ringworm of the scalp and tinea tonsurans. In the US and other regions of the world, the incidence of tinea capitis is increasing.

The tinea capitis infection is the most common cause of hair loss in children. Children with tinea capitis usually have patchy hair loss with some broken-off hairs visible just above the surface of the scalp. The patches of hair loss are usually round or oval, but sometimes irregular. Sometimes the hairs are broken right at the surface, and look like little black dots on the scalp. Sometimes gray flakes or scales are seen.

Alopecia Areata is the sudden appearance of round or oval patches of hair loss. These patches are completely slick bald or smooth without any signs of inflammation, scaling, or broken hairs. They appear literally overnight, or sometimes over a few days.

Alopecia areata is thought to be caused by the body's immune system attacking the hair follicles. At any given moment, about 1 in 1,000 children has alopecia areata. About 25% of these children will also have pitting or ridging of the nails.

About 5% of children with alopecia areata will go on to develop alopecia totalis—the loss of all the hair on the scalp. Some of these will develop alopecia universalis—the complete loss of body hair.

Alopecia areata is an unpredictable disease and even with complete remission it is possible for it to occur again throughout your child's lifetime.

Trauma to the hair shaft is another common cause of hair loss in children. Often the trauma is caused by traction (consistently worn tight braids, pony-tails, etc.) or by friction (rubbing against a bed or wheelchair for example). It can also be caused by chemicals burns.

Another misunderstood cause of trauma hair loss is called trichotillomania, the habit of twirling or plucking the hair. Trichotillomania is thought to be an obsessive-compulsive disorder that can be extremely difficult to treat since the patient usually feels compelled to pluck their hair. The hair loss is patchy, and characterized by broken hairs of varying length. Within the patches, hair loss is not complete. Some children with trichotillomania also have trichophagy—the habit of eating the hair they pluck. These patients can develop abdominal masses consisting of balls of undigested hair. As long as the hair trauma was not severe or chronic enough to cause scarring, the hair will regrow when the trauma is stopped.

Telogen effluvium is another common cause of hair loss in children. To understand telogen effluvium, one must understand a hair's normal life cycle. An individual hair follicle has a long growth phase, producing steadily growing hair for 2 to 6 years (on average 3 years). This is followed by a brief transitional phase (about 3 weeks) when the hair follicle degenerates. This in turn is followed by a resting phase (about 3 months) when the hair follicle lies dormant. This last phase is called the telogen phase. Following the telogen phase, the growth phase begins again—new hairs grow and push out the old hair shafts. The whole cycle repeats. For most people, 80% to 90% of the follicles are in the growth phase, 5% are in the brief transition phase, and 10% to 15% are in the telogen phase. Each day about 50-150 hairs are shed and replaced by new hairs. In telogen effluvium, something happens to interrupt this normal life cycle and to throw many or all of the hairs into the telogen phase. Between 6 and 16 weeks later, partial or complete baldness appears. Many different events can cause telogen effluvium, including, extremely high fevers, surgery under general anesthesia, excess vitamin A, severe prolonged emotional stress such as a death of a loved one, severe injuries and the use of certain prescription medication such as accutane for acne.

Androgenetic Alopecia (AGA) also known as male pattern baldness or female pattern baldness. It is a thinning of the hair to an almost transparent state, in both men or women. It is thought to be a hereditary form of hair loss and is the most common type of progressive hair loss.

Alopecia—Androgenetic in Men

According to the American Hair Loss Association, androgenetic alopecia or common male pattern baldness (MPB) accounts for most cases of hair loss in men. By the age of thirty-five two-thirds of American men will experience some degree of appreciable hair loss, and by the age of fifty approximately 85% of men have significantly thinning hair. Approximately twenty five percent of men who suffer with male pattern baldness begin the painful process before they reach the age of twenty-one.

Contrary to societal belief, most men who suffer from male pattern baldness are extremely unhappy with their situation and would do anything to change it. Hair loss affects every aspect of the hair loss sufferer's life. It affects interpersonal relationships as well as the professional lives of those suffering. It is not uncommon for men to change their career paths because of their hair loss.

Androgenic alopecia or male pattern baldness (MPB) is responsible for the vast majority of hair loss in men. While there are many possible reasons people lose their hair, including serious disease, reaction to certain medications, and in rare cases extremely stressful events, most hair loss in men can be blamed on heredity.

What male pattern baldness sufferers are actually inheriting are hair follicles with a genetic sensitivity to Dihydrotestosterone (DHT). Hair follicles that are sensitive to DHT begin to miniaturize, shortening the lifespan of each hair follicle affected. Eventually, these affected follicles stop producing cosmetically acceptable hair.

Male pattern baldness is generally characterized with the onset of a receding hairline and thinning crown. Hair in these areas including the temples and mid-anterior scalp appear to be the most sensitive to DHT. This pattern eventually progresses into more apparent baldness throughout the entire top of the scalp, leaving only a rim or "horseshoe" pattern of hair remaining in the more advanced stages of MPB. For some men even this remaining rim of hair can be affected by DHT.

Dihydrotestosterone (DHT) is a derivative or by-product of testosterone. Testosterone converts to DHT with the aid of the enzyme Type II 5-alpha-reductase, which is held in the hair follicle's oil glands. While the entire genetic process of male pattern baldness is not completely understood, scientists do know that DHT shrinks hair follicles, and that when DHT is suppressed, hair follicles continue to thrive. Hair follicles that are sensitive to DHT must be exposed to the hormone for a prolonged period of time in order for the affected follicle to complete the miniaturization process. Today, with proper intervention this process can be slowed or even stopped if caught early enough.

According to the American Hair Loss Association The following two treatments have been clinically proven to successfully treat hair loss in men to varying degrees.

Finasteride, Proscar/Propecia

Finasteride is the generic name for the brand name drugs Proscar and Propecia. Finasteride was originally developed by Merck as a drug to treat enlarged prostate glands (Proscar). During the trials on men with prostate problems an intriguing side effect of hair growth was observed. Since finasteride had already been approved by the FDA to treat enlarged prostates in men, Merck and Company decided to pursue the possibility of developing finasteride as the first pill to treat male pattern baldness.

On Dec. 22, 1997 the FDA approved a 1 mg dose of finasteride for the treatment of androgenic alopecia in men (male pattern baldness). Propecia is the first drug in history to effectively treat male pattern baldness in the vast majority of men who use it.

How Propecia/Finasteride Works:

Finasteride's hair-raising success is due to its ability to specifically inhibit Type II 5-alpha-reductace, the enzyme that converts testosterone into a more potent androgen dihydrotestosterone (DHT). Propecia's 1 mg dose of finasteride can effectively lower DHT levels by as much as 60% when taken daily. It is DHT that shrinks or miniaturizes the hair follicle, which eventually leads to baldness. This 60% reduction in DHT has proven to stop the progression of hair loss in 86% of men taking the drug during clinical trials. 65% of trial participants experienced what was considered a substantial increase in hair growth.

At this point, the only truly effective medically proven way to arrest the hair loss process is to lower DHT levels. The American Hair Loss Association recommends finasteride as the first line of attack for all men interested in treating their male pattern baldness.

Minoxidil (Loniten)

Minoxidil (loniten) was the first drug approved by the FDA for the treatment of male pattern baldness. For many years, minoxidill, in pill form, was widely used to treat high blood pressure. Just like finasteride researchers discovered a very interesting side effect of the drug. People taking the medication were growing hair in unexpected places like on their cheeks and the back of their hands, some even grew hair on their foreheads.

Some enterprising researchers had the notion that applying minoxidil topically, directly on the head, might grow hair on balding areas. Well it did this to varying degrees depending on the extent of the hair loss. For it's time, this treatment was revolutionary.

While minoxidil has been clinically proven to slow the progression of hair loss and regrow some hair, most informed experts see it as a relatively marginally effective drug in the fight against hair loss. Since minoxidil has no effect on the hormonal process of hair loss its positive effects are at best temporary and usually yield somewhat disappointing long-term results.

With that said, The American Hair Loss Association still recommends the drug for those who have not responded favorably to finasteride treatment or for those who would like to add another product to their regimen. The AHLA does not recommend minoxidil as the first line of attack for men suffering with male pattern baldness, but does recognize it as an effective treatment for a small percentage of its users.

In many cases minoxidil and finasteride fail. In other cases there are medical reasons to want to avoid their use, and/or the risk of side effects. In such cases, an alternative therapy is needed.

Alopecia—Androgenetic in Women

According to the American Hair Loss Association:

Mistakenly thought to be a strictly male disease, women actually make up forty percent of American hair loss sufferers. Hair loss in women can be absolutely devastating for the sufferer's self image and emotional well being.

Unfortunately, society has forced women to suffer in silence. It is considered far more acceptable for men to go through the same hair loss process. Even more unfortunately, the medical community also treats the issue of women's hair loss as if it were nonexistent. Since hair loss doesn't appear to be life threatening, most physicians pay little attention to women's complaints about hair loss and essentially tell their patients that "it's no big deal", and that "you'll just have to live with it."

Of course what these physicians don't seem to realize is that the psychological damage caused by hair loss and feeling unattractive can be just as devastating as any serious disease, and in fact, can take an emotional toll that directly affects physical health.

The American Hair Loss Association recognizes that hair loss is women is a serious life altering condition that can no longer be ignored by the medical community and society as a whole.

Hair loss can be temporary or long lasting. Temporary hair loss can be easy to fix when its cause is identified and dealt with, or difficult when it is not immediately clear what the cause is. Hair loss that could possibly have been temporary, may become long lasting as a result of an incorrect diagnosis. The potential for such misdiagnoses is perhaps the most frustrating aspect of hair loss for women.

Alopecia is the medical term for excessive or abnormal hair loss. There are different kinds of alopecia. What all hair loss has in common, whether it's in men or women, is that it is always a symptom of something else that's gone wrong in your body. Your hair will remain on your head where it belongs if hormone imbalance, disease, or some other condition is not occurring. That condition may be as simple as having a gene that makes you susceptible to male or female pattern baldness or one of the forms of alopecia areata, or it may be as complex as a whole host of diseases. Fortunately, hair loss may also be a symptom of a short-term event such as stress, pregnancy, and the taking of certain medications. In these situations, hair will often (though not always) grow back when the event has passed. Substances, including hormones, medications, and diseases can cause a change in hair growth, shedding phases and in their durations. When this happens, synchronous growth and shedding occur. Once the cause is dealt with, many times hairs will go back to their random pattern of growth and shedding, and the hair loss problem stops. Unfortunately, for some women, hair loss becomes a life long struggle.

Dihydrotestosterone (DHT), a derivative of the male hormone testosterone, is the enemy of hair follicles on your head. Simply put, under certain conditions DHT wants those follicles dead. This simple action is at the root of many kinds of hair loss, so we'll address it first.

Androgenetic alopecia, commonly called male or female pattern baldness, was only partially understood until the last few decades. For many years, scientists thought that androgenetic alopecia was caused by the predominance of the male sex hormone, testosterone, which women also have in trace amounts under normal conditions. While testosterone is at the core of the balding process. DHT is thought to be the main culprit.

Testosterone converts to DHT with the aid of the enzyme Type II 5-alpha reductase, which is held in a hair follicle's oil glands. Scientists now believe that it's not the amount of circulating testosterone that's the problem but the level of DHT binding to receptors in scalp follicles. DHT shrinks hair follicles, making it impossible for healthy hair to survive.

The hormonal process of testosterone converting to DHT, which then harms hair follicles, happens in both men and women. Under normal conditions, women have a minute fraction of the level of testosterone that men have, but even a lower level can cause DHT-triggered hair loss in women. And certainly when those levels rise. DHT is even more of a problem. Those levels can rise and still be within what doctors consider "normal" on a blood test, even though they are high enough to cause a problem. The levels may not rise at all and still be a problem if you have the kind of body chemistry that is overly sensitive to even its regular levels of chemicals, including hormones.

Since hormones operate in the healthiest manner when they are in a delicate balance, the androgens, as male hormones are called, do not need to be raised to trigger a problem. Their counterpart female hormones, when lowered, give an edge to these androgens, such as DHT. Such an imbalance can also cause problems, including hair loss.

Hormones are cyclical. Testosterone levels in some men drop by 10 percent each decade after thirty. Women's hormone levels decline as menopause approaches and drop sharply during menopause and beyond. The cyclic nature of both our hair and hormones is one reason hair loss can increase in the short term even when you are experiencing a long-term slowdown of hair loss (and a long-term increase in hair growth) while on a treatment that controls hair loss.

Androgenetic Alopecia

The majority of women with androgenic alopecia have diffuse thinning on all areas of the scalp. Men on the other hand, rarely have diffuse thinning but instead have more distinct patterns of baldness. Some women may have a combination of two pattern types. Androgenic alopecia in women is due to the action of androgens, male hormones that are typically present in only small amounts. Androgenic alopecia can be caused by a variety of factors tied to the actions of hormones, including, ovarian cysts, the taking of high androgen index birth control pills, pregnancy, and menopause. Just like in men the hormone DHT appears to be at least partially to blame for the miniaturization of hair follicles in women suffering with female pattern baldness. Heredity plays a major factor in the disease.

Telogen Effluvium (TE)

When your body goes through something traumatic like childbirth, malnutrition, a severe infection, major surgery, or extreme stress, many of the 90 percent or so of the hair in the anagen (growing) phase or catagen (resting) phase can shift all at once into the shedding (telogen) phase. About 6 weeks to three month after the stressful event is usually when the phenomenon called telogen effluvium can begin. It is possible to lose handful of hair at time when in full-blown telogen effluvium. For most who suffer with TE complete remission is probable as long as severely stressful events can be avoided. For some women however, telogen effluvium is a mysterious chronic disorder and can persist for months or even years without any true understanding of any triggering factors or stressors.

Anagen Effluvium

Anagen effluvium occurs after any insult to the hair follicle that impairs its mitotic or metabolic activity. This hair loss is commonly associated with chemotherapy. Since chemotherapy targets your body's rapidly dividing cancer cells, your body's other rapidly dividing cells such as hair follicles in the growing (anagen) phase, are also greatly affected. Soon after chemotherapy begins approximately 90 percent or more of the hairs can fall out while still in the anagen phase.

The characteristic finding in anagen effluvium is the tapered fracture of the hair shafts. The hair shaft narrows as a result of damage to the matrix. Eventually, the shaft fractures at the site of narrowing and causes the loss of hair.

Traction Alopecia

This condition is caused by localized trauma to the hair follicles from tight hairstyles that pull at hair over time. If the condition is detected early enough, the hair will regrow. Braiding, cornrows, tight ponytails, and extensions are the most common styling causes.

Since the "pill" was approved by the FDA in 1960, oral contraceptives have become one of the most popular forms of birth control used today.

Millions of women are prescribed the pill each year in this country, but very few are aware that oral contraceptives are a common trigger of hair loss for many who use them.

The "pill" suppresses ovulation by the combined actions of the hormones estrogen and progestin or in some cases progestin alone. Women who are predisposed to hormonal related hair loss or who are hypersensitive to the hormonal changes taking place in their bodies can experience hair loss to varying degrees while on the pill or more commonly, several weeks or months after stopping the pill.

The American Hair Loss Association recommends that all women interested in using oral contraceptives for the prevention of conception should only use low-androgen index birth control pills, and if there is a strong predisposition for genetic hair loss in your family we recommend the use of another non-hormonal form of birth control.

The Women are in a "Catch-22" position when it comes to drug treatments for androgenetic alopecia. While many drugs may work to some degree for some women, doctors are reluctant to prescribe them, and drug companies aren't exactly falling over themselves to test existing or new drugs specifically for their ability to prevent and treat female pattern baldness.

Physicians are reluctant to use systemic treatment (a pill or other form of internal treatment that affects your entire system) unless they know that the hair loss is due to an excess of androgen in the system or a sensitized "over-response" to the so-called "normal" amounts of androgen in the system. That's because these systemic treatments may lower the body's androgen levels. Therefore, physicians often choose topical treatments (those that are applied directly to the scalp).

The best results from treatment happen when you begin treatment as soon as possible after the hair loss begins because prolonged androgenetic alopecia may destroy many of the hair follicles. The use of anti-androgens after prolonged hair loss will at least help prevent further hair loss and encourage some hair regrowth from those follicles that have been dormant but are still viable, Stopping treatment will result in the hair loss resuming if the androgens aren't kept in check in some other way. Maintaining your vitamin and mineral levels helps while you're on anti-androgen medications.

As always, treatments have the best chance of being effective if they are geared to the cause of the hair loss as well as to triggering hair growth.

Currently there is only one FDA approved treatment for female pattern hair loss.

Minoxidil 2% Topical Treatment

Minoxidil was first used in tablet form as a medicine to treat high blood pressure (an antihypertensive). It was noticed that patients being treated with minoxidil experienced excessive hair growth (hypertrichosis) as a side effect. Further research showed that applying a solution of minoxidil directly to the scalp could also stimulate hair growth. The amount of minoxidil absorbed through the skin into the bloodstream is usually too small to cause internal side effects.

Women with diffuse androgenetic alopecia can use minoxidil and it actually seems to be more effective for women compared to men. The makers of minoxidil recommend women only use the 2% concentration of minoxidil and not 5%. The makers of minoxidil have not received FDA approval for promoting 5% minoxidil or minoxidil extra strength for use by women. Many dermatologists do prescribe minoxidil 5% for women with androgenetic alopecia if used under their supervision. Some small clinical trials have been conducted on 5% minoxidil for androgenetic alopecia in women showing that indeed the 5% solution is significantly more effective in both retaining and regrowing hair than the 2% solution.

In clinical studies of mostly white women aged 18-45 years with mild to moderate degrees of hair loss, the following response to minoxidil was reported: 19% of women reported moderate hair growth after using minoxidil for 8 months (19% had moderate regrowth: 40% had minimal regrowth). This compares with 7% of women reporting moderate hair regrowth after using the placebo, the liquid without the active ingredient in it, for 8 months (7% had moderate regrowth, 33% had minimal regrowth).

Propecia/Proscar

The drug finasteride inhibits the enzyme 5-alpha reductase, thereby inhibiting the production of prostate-harming, follicle killing DHT. It was first marketed to treat the prostate under the brand name Proscar in 5 mg pills. In 1998, a 1 mg version with the brand name Propecia entered the market as the first pill approved by the FDA for men's hair loss. It works quite well for most men in both preventing hair loss and triggering regrowth, and it may work for some women, although women must not take it if they are pregnant and must not get pregnant while on the drug because of the risk of birth defects in a male fetus. Less than 2 percent of men experience transient sexual side effects including erectile and libido difficulties. In women these side effects do not occur.

In many cases minoxidil and finasteride fail. In other cases there are medical reasons to want to avoid their use, and/or the risk of side effects.

Other forms of alopecia are Cicatricial Alopecias (Scarring Alopecias) and Alopecia mucinosa

SUMMARY OF THE INVENTION

In some exemplary embodiments of the invention there is provided a treatment method including: (a) identifying a subject in need of treatment for androgenic alopecia (AGA), and (b) orally administering a physiologically effective amount of cepharanthine (CEP) to said subject according to a dosage regimen. In some embodiments the dosing regimen is once per day. Alternatively or additionally, in some embodiments the dosing regimen is once every other day. Alternatively or additionally, in some embodiments physiologically effective amount of CEP is 0.5 to 5.0 mg/day on average. Alternatively or additionally, in some embodiments the physiologically effective amount of cepharanthine is 0.5 to 2 mg/day on average. Alternatively or additionally, in some embodiments the physiologically effective amount of cepharanthine is 0.75 to 1.5 mg/day on average.

In some exemplary embodiments of the invention there is provided a treatment kit comprising: (a) a plurality of oral dosage forms of cepharanthine (CEP); and (b) packaging material comprising instructions for use in the treatment of androgenic alopecia (AGA) according to a dosage regimen. In some embodiments the instructions include a disclaimer that CEP is not effective and/or not approved for treatment of AGA.

Alternatively or additionally, in some embodiments each of the oral dosage forms comprises 0.5 to 5.0 mg CEP. Alternatively or additionally, in some embodiments each of the oral dosage forms comprises 0.5-1.0 mg cepharanthine. Alternatively or additionally, in some embodiments the dosing regimen is once per day or less frequent. Alternatively or additionally, in some embodiments the dosing regimen is once every other day. Alternatively or additionally, in some embodiments the kit is labeled as a nutritional supplements or food supplement. Alternatively or additionally, in some embodiments the oral dosage forms are provided as capsules, pills, lozenges, dragees, buccal or sublingual form tablets, liquid form, lipid dissolved or suspended form or chewing gum.

In some exemplary embodiments of the invention there is provided a method of manufacture comprising: (a) assembling a plurality of dosage forms of cepharanthine (CEP); and (b) packaging said plurality of dosage forms with instructions for use in the treatment of androgenic alopecia (AGA) according to a dosage regimen. In some embodiments the instructions include a disclaimer that CEP is not effective and/or not approved for treatment of AGA. Alternatively or additionally, in some embodiments of the dosage forms comprises 0.5 to 5.0 mg CEP. Alternatively or additionally, in some embodiments each of the dosage forms comprises 0.5-1.0 mg cepharanthine. Alternatively or additionally, in some embodiments the method includes labeling the packaging material to indicate that the CEP is a nutritional supplements or food supplement. Alternatively or additionally, in some embodiments the method includes preparing said dosage forms. According to some exemplary embodiments of the invention the dosage forms are oral, e.g. capsules, pills, lozenges, dragees, buccal or sublingual form tablets, liquid form, lipid dissolved or suspended form or chewing gum.

DETAILED DESCRIPTION OF EXEMPLARY EMBODIMENTS OF THE INVENTION

Cepharanthine (CEP) is a naturally occurring plant based alkaloid (isolated primarily from the *stephania* spp) used to treat inflammatory conditions. CEP has successfully been used to treat a diverse range of medical conditions, including radiation-induced leukopenia, idiopathic thrombocytopenic purpura, alopecia areata, alopecia pityrodes, venomous snakebites, xerostomia, sarcoidosis, refractory anemia and various cancer-related conditions. No safety issues have been observed with CEP, and side effects are very rarely reported.

Cepharanthine has not been reported to be beneficial for androgenetic alopecia. The mechanism of hair loss in androgenetic alopecia is very different from that in alopecia areata or alopecia pityrodes (which is primarily a skin disorder).

When treating alopecia areata or alopecia pityrodes, it is commonly used in divided doses—2-3 times a day after meals. It is generally sold as a pharmaceutical product required a physician's prescription.

Experiments and Results

We have surprisingly discovered that CEP is effective in treating androgenetic alopecia in both males and females. It is effective when dosed once daily or even once every other day, both of which make compliance much easier than dividing the doses into greater frequency. It is effective without regard to consumption following meals.

The description of the experiments and their results are presented in the 4 tables below. In these experiments the subjects self-administered CEP for at least 6 months.

TABLE 1

| Study Name: | Androgenetic Alopecia Males Arm 1 | Androgenetic Alopecia Males Arm 2 | Androgenic Alopecia Females |
|---|---|---|---|
| Intervention | Cepharanthine 2 mg once daily | Cepharanthine 2 mg once every other day | Cepharanthine 2 mg daily |
| Number of Subjects | 40 | 40 | 30 |
| Treated | 20 | 20 | 15 |
| Controls | 20 | 20 | 15 |
| Duration of Treatment | 6 months | 6 months | 6 months |
| Hamilton-Norwood Classification (Male)/Ludwig Scale (females) | 2-5 | 2-5 | II-2 - Frontal |
| Age Hair Loss First Seen | 23.8 +− 5.1 | 26.3 +− 5.6 | 22.1 +− 7.6 |
| White Hair - None | 21 | 28 | 17 |
| White Hair - Few | 14 | 11 | 18 |
| White Hair - Many | 5 | 1 | 3 |
| Failed finasteride | 20 | 18 | 28 |
| Failed minoxidil | 24 | 22 | 26 |
| Failed other treatments | 30 | 35 | 27 |
| Dandruff | None | None | None |
| Global Photographic Assessement Method (Omnia System) Global photographs of midline and vortex of baseline vs 6 months were used for this evaluation. The regions assessed were the vertex and superio-frontal regions, as well as overall head. The validated improvement scale is used in all clinical hair studies and spans from −3 = greatly decreased to +3 greatly increased. | At 6 months, 16 of 20 active subjects demonstrated improvement relative to baseline - see Table 2 | At 6 months, 14 of 20 active subjects demonstrated improvement relative to baseline - see Table 3 | At 6 months, 11 of 15 active subjects demonstrated improvement relative to baseline - see Table 4 |

TABLE 2

| | Androgenetic Alopecia Male Arm 1 | |
|---|---|---|
| Score | Placebo | Active |
| Greatly decreased | 0 | 0 |
| Moderately decreased | 1 | 0 |
| Slightly decreased | 15 | 1 |
| No change | 4 | 3 |
| Slightly increased | 0 | 8 |
| Moderately increased | 0 | 7 |
| Greatly increased | 0 | 1 |

TABLE 3

| | Androgenetic Alopecia Male Arm 2 | |
|---|---|---|
| Score | Placebo | Active |
| Greatly decreased | 0 | 0 |
| Moderately decreased | 2 | 0 |
| Slightly decreased | 12 | 2 |
| No change | 6 | 4 |
| Slightly increased | 0 | 9 |
| Moderately increased | 0 | 5 |
| Greatly increased | 0 | 0 |

TABLE 4

| | Androgenetic Alopecia Females | |
|---|---|---|
| Score | Placebo | Active |
| Greatly decreased | 0 | 0 |
| Moderately decreased | 2 | 0 |
| Slightly decreased | 9 | 1 |
| No change | 3 | 3 |
| Slightly increased | 1 | 8 |
| Moderately increased | 0 | 2 |
| Greatly increased | 0 | 1 |

We also tested CEP in subjects suffering from different forms of hair loss such as congenital alopecia (atrichia congenita, hypotrichosis congenita etc), chronic telogen effluvium and traction alopecia without any beneficial effects.

Since our results showed a therapeutic effect limited to androgenetic (androgenic) alopecia, this leads us to believe that CEP may possess some influencing effect specific to androgenetic alopecia (in addition to its well known effect against inflammatory/autoimmune caused alopecia). While CEP has been reported in a single study to stimulate cortisone production (which may explain its well known effect against inflammatory/autoimmune caused alopecia), we have found no studies of any possible modulation of DHT as result of cepharanthine use.

In some of the successfully treated subjects, we noticed great improvement in pigmentation—with hair becoming darker or in a few cases becoming completely dark after having been white pre-treatment.

Some users were not perfectly compliant, sometimes skipping their daily doses. Since therapeutic benefit was noted in those users too, it means that the effective dose may be as little as 0.5 mg CEP a day. The expected effective dose range is from about 0.5 mg per day to about 100 mg per day.

In some embodiments not less than about 0.5 mg, not less than about 1 mg a day or not less than about 2 mg a day are used, in at least a single daily dose, or in at least a single dose every other day.

In some embodiments length of treatment is at least 1 month, at least 2 months, at least 3 months, at least 4 months, at least 5 months, at least 6 months, at least 9 months, at least 12 months, at least 18 months or at least 24 months.

In some embodiments, CEP is provided as the isolated pure alkaloid (with a purity level of >92%) encapsulated or prepared as a pill with well known inert ingredients as fillers/binders.

In some embodiments, a plant extract or plant powder is used, generally of the *stephania* spp species containing cepharanthine, but where the CEP content is concentrated to more than its naturally occurring concentration, and able to provide the therapeutic dose of CEP (about 1 mg or about 2 mg) in at least a single dose.

In some embodiments, the CEP or CEP-containing plant extract or powder is used in a formulation that contains ingredients known to support hair synthesis. These can include all or some of: Vitamin E, 1-taurine, Vitamin B6, Zinc salts/complexes, 1-cysteine, Vitamin B1, Vitamin B2, Vitamin B5, Vitamin B12, biotin, copper, selenium. In some embodiments, the CEP or CEP-containing plant extract or powder is used in a formulation that contains ingredients known to support hair growth and/or treat androgenetic alopecia such as serenoa repens, finasteride, minoxidil etc. In some cases synergistic activity may occur.

In some embodiments, CEP is the only active ingredient.

In some embodiments, CEP is used in oral capsule form, in oral pill form, in lozenge form, in buccal form, in sublingual form, in liquid form, in lipid dissolved or suspended form, in chewing gum form etc.

In some embodiments, treatment packs or kits are provided which include the dosage forms containing CEP together with instructions for use. In some embodiments, the treatment packs will include single doses and in some embodiments they may include a multiplicity of doses. In some embodiments the kits or treatment packs may include at least a 30 day, at least a 60 day, at least a 120 day, at least a 150 day, at least a 180 day or at least a 360 day supply for a single user.

In some embodiments, the invention is provided as a pharmaceutical composition. In some embodiments it is provided as a nutritional supplements or food supplement. In some embodiments, the invention will not require a physician's prescription.

In some embodiments, especially where the product containing CEP may be sold as a non-prescription item where therapeutic claims are not permitted to be provided simultaneously with the product containing CEP, different forms may be used to disseminate details of the product and its therapeutic benefits to potential clients. This may include newspaper advertising, media advertising, electronic, email or social media based advertising and similar methods as typically used to market products to consumers.

Alternatively, or additionally, features used to describe a method can be used to characterize a composition or kit and features used to describe a composition or kit can be used to characterize a method.

It should be further understood that the individual features described hereinabove can be combined in all possible combinations and sub-combinations to produce additional embodiments of the invention. The examples given above are exemplary in nature and are not intended to limit the scope of the invention which is defined solely by the following claims.

Each recitation of an embodiment of the invention that includes a specific feature, part, component, module or process is an explicit statement that additional embodiments of the invention not including the recited feature, part, component, module or process exist.

Alternatively or additionally, various exemplary embodiments of the invention exclude any specific feature, part, component, module, process or element which is not specifically disclosed herein. For example, many embodiments of the invention do not include chromene.

The invention claimed is:

1. A treatment method comprising:
   (a) identifying a subject in need of treatment for androgenic alopecia (AGA),
   (b) orally administering an amount of cepharanthine (CEP) effective in treating AGA to said subject according to a dosage regimen;
   wherein said CEP is administered without chromene.

2. A method according to claim 1, wherein said dosing regimen is once per day.

3. A method according to claim 1, wherein said dosing regimen is once every other day.

4. A method according to claim 1, wherein said amount of CEP is 0.5 to 5.0 mg/day on average.

5. A method according to claim 1, wherein said amount of CEP is 0.5 to 2 mg/day on average.

6. A method according to claim 1, wherein said amount of CEP is 0.75 to 1.5 mg/day on average.

7. A method according to claim 1, wherein said amount of CEP is 0.5 to 100 mg/day on average.

8. A method according to claim 1, wherein said CEP is provided as a plant extract or plant powder of *Stephania* spp species with the CEP content concentrated to more than its natural concentration.

9. A treatment method comprising:
   (a) identifying a subject in need of hair darkening,
   (b) orally administering an amount of cepharanthine (CEP) effective in darkening hair to said subject according to a dosage regimen.

10. A method according to claim 9, wherein said dosing regimen is once per day.

11. A method according to claim 9, wherein said dosing regimen is once every other day.

12. A method according to claim 9, wherein said amount of CEP is 0.5 to 5.0 mg/day on average.

13. A method according to claim 9, wherein said amount of CEP is 0.5 to 2 mg/day on average.

14. A method according to claim 9, wherein said amount of CEP is 0.75 to 1.5 mg/day on average.

15. A method according to claim 9, wherein said amount of CEP is 0.5 to 100 mg/day on average.

16. A treatment method comprising:

orally administering an amount of cepharanthine (CEP) effective in treating androgenic alopecia (AGA) to a subject suffering from AGA according to a dosage regimen without administering chromene to said subject.

17. A method according to claim 1, wherein said amount of CEP is 0.5 to 5.0 mg/day on average.

18. A method according to claim 1, wherein said amount of CEP is 0.5 to 2 mg/day on average.

19. A method according to claim 1, wherein said amount of CEP is 0.5 to 100 mg/day on average.

20. A method according to claim 1, wherein said CEP is provided as a plant extract or plant powder of *Stephania* spp species with the CEP content concentrated to more than its natural concentration.

\* \* \* \* \*

UNITED STATES PATENT AND TRADEMARK OFFICE
CERTIFICATE OF CORRECTION

PATENT NO.        : 9,855,204 B1
APPLICATION NO.   : 15/387676
DATED             : January 2, 2018
INVENTOR(S)       : Moshe Rogosnitzky Page 1 of 1

It is certified that error appears in the above-identified patent and that said Letters Patent is hereby corrected as shown below:

On the Title Page

In item (71) Applicant and item (72) Inventor, for the city "Kiryay Yearim" each occurrence should read --Kiryat Yearim--.

In the Claims

At Column 13, Lines 7 to 13 in each of Claims 17, 18, 19 and 20 each occurrence of "A method according to claim 1," should read --A method according to claim 16,--.

Signed and Sealed this
First Day of May, 2018

Andrei Iancu
*Director of the United States Patent and Trademark Office*